United States Patent
Oraby

[19]

[11] Patent Number: 6,072,314
[45] Date of Patent: Jun. 6, 2000

[54] NMR INTERPRETATION TECHNIQUE USING ERROR MINIMIZATION WITH VARIABLE T2 CUTOFF

[75] Inventor: Moustafa Oraby, Houston, Tex.

[73] Assignee: Halliburton Energy Services, Inc., Houston, Tex.

[21] Appl. No.: 08/931,539

[22] Filed: Sep. 16, 1997

[51] Int. Cl.$^7$ .................................................. G01V 3/00
[52] U.S. Cl. ........................................................ 324/303
[58] Field of Search ............................................ 324/303

[56] References Cited

U.S. PATENT DOCUMENTS

| | | | |
|---|---|---|---|
| 4,413,512 | 11/1983 | Zemanek, Jr. | 73/152.08 |
| 4,773,264 | 9/1988 | Herron | 73/152 |
| 5,023,551 | 6/1991 | Kleinberg et al. | 324/303 |
| 5,498,960 | 3/1996 | Vinegar et al. | 324/303 |

OTHER PUBLICATIONS

NMR Logging of Natural Gas Reservoirs, SPWLA 36$^{th}$ Annual Logging Symposium, Jun. 26–29, 1995, by R. Akkurt, et al.

Pore–size Distribution and NMR in Microporous Cherty Sandstones, SPWLA Thirtieth Annual Logging Symposium, Jun. 11–14, 1989, by W.E. Kenyon, et al.

Relations Between Pore Size Fluid and Matrix Properties and NML Measurements, Society of Petroleum Engineers Journal, Sep. 1979, by J.D. Loren, et al.

Core and Log NMR Measurements of an Iron–Rich, Glauconitic Sandstone Reservoir, SPWLA 36$^{th}$ Annual Loggins Symposium, Jun. 26–29, 1995, by WM. Scott Dodge Sr., et al.

Residual Oil Saturation Measurements in Carbonates with Pulsed NMR Logs, SPWLA 36$^{th}$ Annual Logging Symposium, Jun. 29–29, 1995, by John P. Horkowitz, et al.

A Laboratory Study of Nuclear Magnetic Resonance Relaxation and its Relation to Depositional Texture and Petrophysical Properties, Society of Petroleum Engineers SPE 29886, 1995, by W.E. Kenyon, et al.

*Primary Examiner*—Christine Oda
*Assistant Examiner*—Tiffany A. Fetzner
*Attorney, Agent, or Firm*—Conley, Rose & Tayon

[57] ABSTRACT

This invention provides improved geological formation evaluation, resulting in a more accurate prediction of the location of hydrocarbon. It also increases the yield at those sites. The disclosed method involves determination by a nuclear magnetic resonance tool of a downhole T2 distribution, determination of T2 cutoff valves at discrete points in the borehole, and deriving a variable T2 cutoff time by either linear or non-linear correlations. Derivation of these variable T2 cutoff times provides the likely location of high irreducible water saturation, even where large quantities of movable water reside nearby.

25 Claims, 4 Drawing Sheets

NMR INTERPRETATION TECHNIQUE USING ERROR MINIMIZATION WITH VARIABLE T2 CUTOFF

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

The inexpensive and continued production of hydrocarbons is essential to the maintenance of modem society. In view of a limited world hydrocarbon supply, keeping energy costs low requires a continual improvement in geological formation evaluation and hydrocarbon recovery. This constant quest for improvement requires breakthroughs in well logging technology. Improved formation data logs allow more accurate predictions of where producible hydrocarbon may be found and increase the yield at these sites. Past improvements in the field of hydrocarbon well logging include induction and resistivity tools, acoustic tools, and nuclear tools.

The determination of whether a particular geological formation contains produceable hydrocarbon can be extraordinarily complicated. Initially, it must be determined what, if anything, a sub-surface formation contains. If it contains fluid, it must be determined whether this fluid is water, hydrocarbon, or both. One difficulty encountered by the hydrocarbon industry is its need to retrieve a hydrocarbon stream from the ground that contains only a limited supply of water or brine. Thus, although an area may contain adequate hydrocarbons, excessive water may make it unsuitable for production. Resistivity tools have been useful in determining whether water is present in an hydrocarbon-rich formation. However, the mere presence of sub-surface water does not give a full picture of whether there exists producible hydrocarbon. This also depends upon the character of the detected water. Thus, resistivity tools are not ideal because they indicate merely the presence of water, and cannot indicate its mobility. When underground water comes up-hole with the retrievable hydrocarbons it is known as being free, movable, or reducible. Conversely, when the underground water remains down-hole at the time of production it is known as being bound, immovable, or irreducible. Thus, if one cannot determine the mobility of the underground water, many potentially productive hydrocarbon zones with high irreducible water saturation are bypassed because of fear of excessive water production.

One technology that has proved to be helpful in modem formation evaluation is nuclear magnetic resonance (NMR) technology. This technology assists in the control of water production and identification of pay zones with high irreducible (or bound) water saturation. One such NMR tool is the MRIL® C-type tool, shown in FIG. 1. Also shown is a borehole 150. The MRIL® apparatus is a centralized device containing a permanent magnet and a radio frequency (RF) pulse generator (not shown). The tool as shown has an outer diameter 110 of 6" and a length of about 50'. A slim version of the tool (not shown) has an outer diameter of 4 ½". In an 8" borehole 150, MRIL® depth of investigation 120 is 4 inches. The tool's permanent magnet generates a magnetic field of 2500 gauss (5,000 times the strength of the earth's magnetic field) with a field gradient of 17 gauss/centimeter. When random hydrogen nuclei interact with the applied magnetic fields, measurable signals are produced. The primary field of the permanent magnet aligns the hydrogen nuclei in one direction. The tool then uses its radio frequency generator to pulse a second magnetic field perpendicular to the permanent magnet's primary field. This RF generator operates at the Larmor frequency to rotate the nuclei 90° with respect to the alignment induced by the permanent magnet. After the RF pulse is turned off, the nuclei gradually dephase or disorder, causing the signal to decay. MRIL® operates on three close frequencies, which improves the signal to noise ratio and increases the logging speed. The time consumed by the nuclei to completely dephase is called the T2 time, and the time required for the nuclei to return to their initial aligned position is called the T1 time. The T2 time is shorter than the T1 time and has been chosen as the time measured by the current MRILX C-type tool.

This T2 time varies from one hydrogen nucleus to another, depending on the location of the hydrogen in the formation. When the hydrogen is located adjacent an underground rock surface, it comprises immovable or bound water. Surface tension holds this water to the rock surface and causes the water to remain downhole. When this bound fluid is affected by the magnetic field of an NMR tool, the rock causes the bound water to have a shorter T2 time. Moveable water, in contrast, lives in the bulk, and not at the surface of a rock. Thus, the T2 time of its hydrogen is unaffected by a rock's surface and so is longer in duration. In this way, movable water may be differentiated from immovable water based on their respective T2 times.

FIG. 2 is a graph illustrating T2 data. T2 data has two important aspects, known as the T2 distribution 200 and the T2 cut-off 210. The T2 cut-off 210 separates the effective porosity into irreducible porosity 220 and moveable porosity 230. In other words, the T2 cut-off is the dividing line between the bound and the free sub-surface water. In contrast, the T2 distribution is used to calculate a distribution of porosity components as a function of their T2 times. Thus, in the T2 distribution, the sum of all porosities whose T2 time is less than the T2 cut-off yields the NMR-bulk volume of irreducible water (MBVI). Similarly, the sum of all porosities whose T2 time is greater than the T2 cut-off furnishes the NMR-determined free fluid index (MFFI). The NMR determined effective formation porocity (MPHI) is then found by adding MBVI and MFFI. The T2 cut-off may not, however, be derived from the T2 distribution. Thus, while the n distribution at a particular depth may be derived by the readings of an NMR tool, the determination of the T2 cutoff for a core sample at this time requires laboratory analysis. Besides porosities, NMR measurements also provide better estimates of formation permeabilities than can be derived from conventional logs.

Nonetheless, prior art NMR measurement techniques suffer from significant shortcomings. For instance, the T2 cut-off time may vary significantly along the length of a well bore. The prior art ignored such variation and arrived at a single T2 cut-off point by averaging the T2 cut-off times from a number of core samples taken from the borewall. Those in the industry would prefer a more accurate method for determining the T2 cut-off times. A more accurate method would allow refinement of geological formation evaluation so that areas containing significant irreducible water could be produced whereas nearby areas containing significant movable water could be avoided. Ideally, such a method would cost a minimal amount. For example, the method would minimize the number of core samples that should be taken and consolidate into one period the time required for expensive production.

SUMMARY OF THE INVENTION

The present invention features a method for improved geological formation evaluation. This method preferably entails drilling a borehole, taking core samples from the borehole, each of the core samples being predominantly one type of rock (such as sandstone, limestone, dolomite, etc.), determining a T2 distribution of a formation lithology surrounding the borehole, determining a T2 cutoff time for each of the core samples, calculating the formation lithology surrounding the borehole, and estimating a variable T2 cutoff time based on the formation lithology. This method preferably includes the use of an NMR tool in the borehole and may use either a linear or nonlinear approach to determining the variable T2 cutoff times.

The present invention also features a device that determines variable T2 cutoff times. Such a device includes means for combining data from a nuclear magnetic resonance tool with other data logs to yield a composite lithology log and means for deriving variable T2 cutoff times based on the composite lithology logs and known T2 cutoff values, either from core or from previous knowledge. Depending upon the characteristics of the formation being analyzed, such a device may use either a linear or a nonlinear correlation to derive the estimated variable T2 cutoff values.

Thus, the present invention comprises a combination of features and advantages which enable it to overcome various problems of prior devices. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENT

Figure 3:
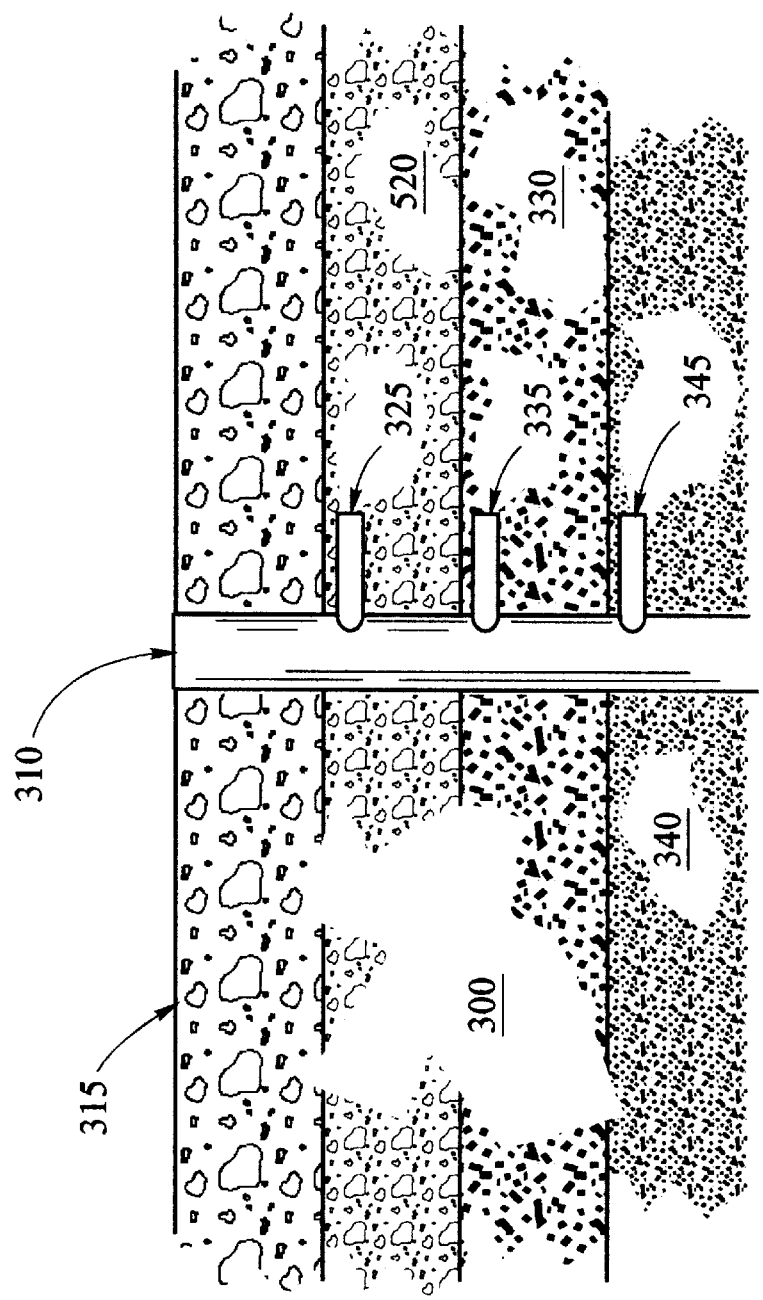
FIG. 3 is an illustration of an borehole drilled in accordance with the present invention.

FIG. 3 is a simplified view of a borehole 310, cut through a complex lithology 300. Complex lithology 300 may be heterogeneous and composed of multiple types of rock. For example, borehole 310 may cut through a first depth 320 corresponding primarily to limestone, a second depth 330 corresponding primarily to dolomite, and a third depth 340 corresponding primarily to sandstone. FIG. 3 also shows three core sample locations 325, 335, and 345. If the oil company has prior knowledge of the $T_2$ cutoff of such single lithology, there is no need to cut core samples. If not, core samples are recommended for better overall $T_2$ cutoff estimation. Upon the drilling of borehole 310, an operator at the surface 315 typically records a mud log (not shown). As is well known in the art, a mud log is a record of information derived from an examination of drilling fluid and cuttings from the formation. As such, the rock composition at any particular depth already is typically made of record. Where rock lithologies are complex, the vertical composition of the cuttings may change up to every half foot. The composition of the subsurface rock at a particular depth as recorded by the mud log may safely be assumed to extend a short distance beyond the borehole wall. Thus, the present invention combines information about lithology, T2 cut-off data, and T2 distribution data to derive a more precise prediction about hydrocarbon productivity at a particular depth. As such, the present invention may indicate the presence of producible hydrocarbon in areas that were previously thought to be barren. Further, this improved accuracy is based on data gathering and procedures that to a great extent were already required in the prior art.

Figure 4:
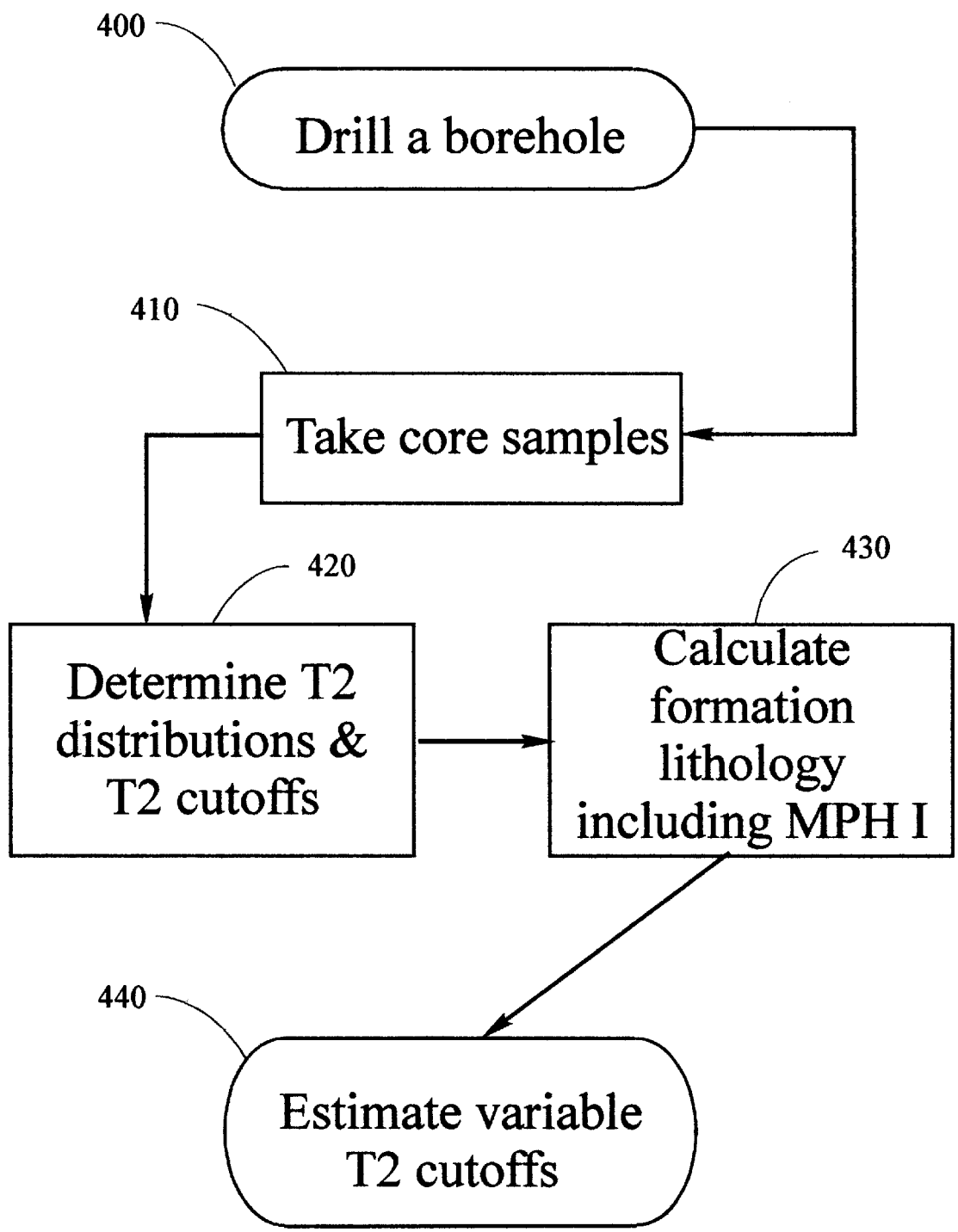
FIG. 4 is a flow chart illustration of the preferred series of steps for deriving estimated variable T2 cutoffs.

FIG. 4 shows a method according to the present invention to increase the precision with which the hydrocarbon industry may predict whether a formation contains producible hydrocarbon. Initially, a borehole is drilled at step 400. A mud log normally is recorded when a borehole is drilled. This mud log may be used to determine the composition of the subsurface lithology. Correspondingly, there is a general indication of the rock type formation at a particular depth. At step 410, a single core sample is taken for each rock type that may be present in the subsurface formation. Each core sample should be of a pure rock type, or as nearly pure as possible (a minimum of about 80% purity is desired). Thus, as shown in FIG. 3, a first core sample 325 corresponding to a first rock type should be taken at a first depth 320, a second core sample 335 corresponding to a second rock type should be taken at a second depth 330, and a third core sample 345 corresponding to a third rock type should be taken at a third depth 340. Since the determination of T2 cut-off times normally requires laboratory analysis, each core sample should then be submitted to a laboratory for determination of its T2 cut-off time at step 420. This laboratory analysis can also include a collection of the point count data to indicate the exact lithology of each core sample.

Figure 1:
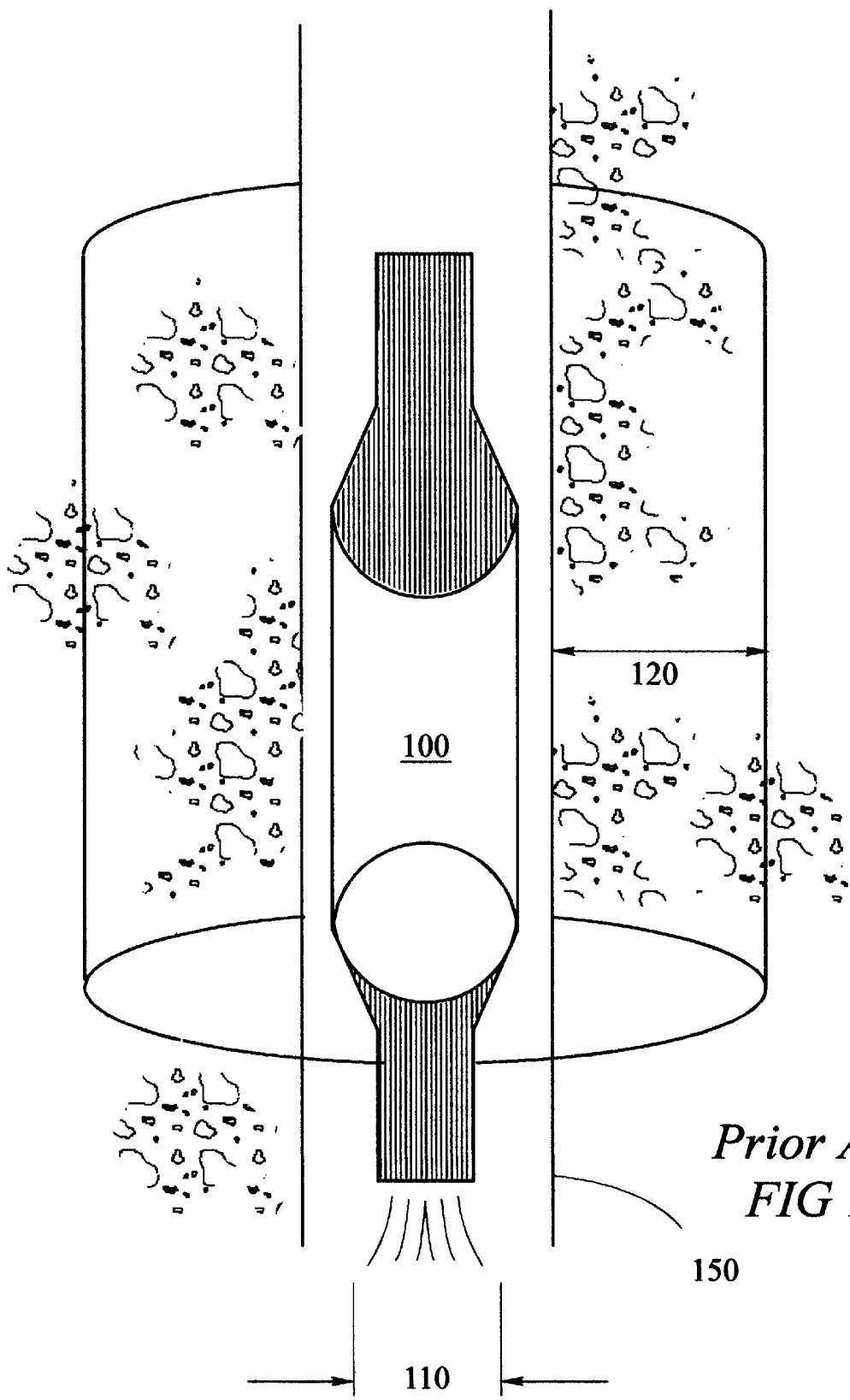
FIG. 1 is an illustration of a downhole NMR device.
Figure 2:
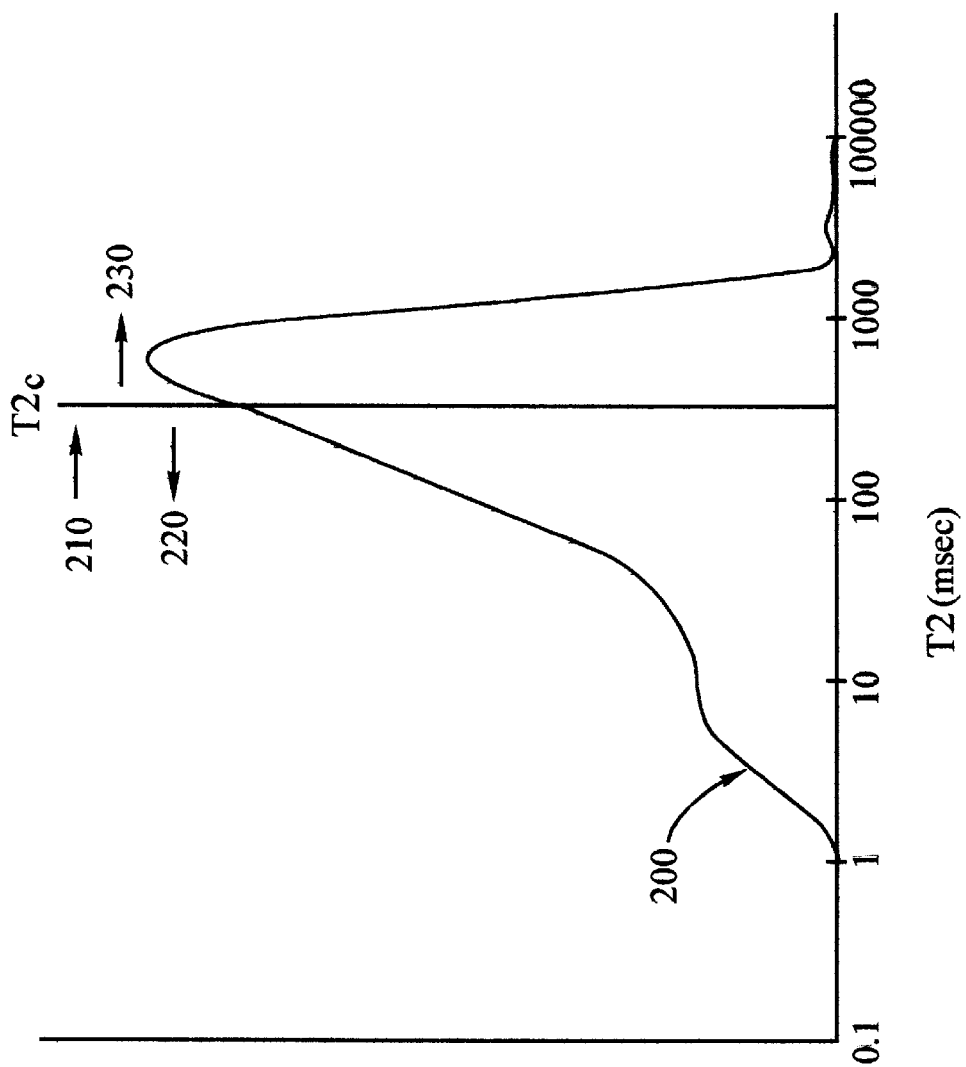
FIG. 2 is a graph depicting one exemplary pair of T2 distribution and T2 cutoff time.

T2 distributions and MPHI should also be collected at step 420. This normally requires insertion of an NMR tool into the borehole 310, such as the MRIL® tool shown in FIG. 1. As already explained, MPHI may be obtained from the T2 distribution. The T2 distribution is found from a train of echoes that are produced upon the decay of the hydrogen nuclei. A complex analysis of the echo train is performed by expressing the $n^{th}$ echo ($E_n$) as an exponential series:

$$E_n = \left( \sum_{i=1}^{8} A_i e^{\frac{t_n}{T_{2i}}} \right) + noise$$

where i=1, 2, ..., 8 and where $T_{2i}=2^{i+1}$ milliseconds are T2 times. Solving the T2 system of equations yields a distribution of the porosities associated with the chosen T2 times. Upon determination of MBVI, MFFI, and MPHI, formation permeability (K) may be derived from Coate's equation:

$$K = \left( \frac{MPHI}{C} \right)^4 \left( \frac{MFFI}{MBVI} \right)^2$$

where C is a term that reflects the correlation between the pore throat and the pore size of the rock. Alternatively, other expressions for formation permeability may be used.

This also is an opportune time for collection of data from other borehole logging tools, such as induction and resistivity tools, acoustic tools, and nuclear tools. Using MPHI and the other available open-hole and cased-hole log response flnction models, the formation lithology may be calculated at step 430. The use of MPHI as an additional variable when deriving formation lithology improves the accuracy of the resulting logs. The derivation of formation lithology at discrete depths in the formation is done by forming a system of equations, comparing the actual logs with the theoretical logs, and applying well known error minimization techniques. To evaluate the precision of the fit between the original logs and the reconstructed logs, the chi-square of the difference between logs is calculated. In this methodology, weighting factors can be applied to the log data, and geological and petrophysical constraints can be imposed. This approach increases the importance of MPHI and derives the final solution accordingly. The algorithm used is based on the simultaneous optimization of a model $f(X,P)$ within a zone at a depth level s. The incoherence function to be optimized is defined as:

$$J = \sum_{S=1}^{N} \sum_{C=1}^{M} \left( \frac{Y_{s,i} - f_i(X_s; P)}{\sigma_{s,i}} \right)^2$$

where MPHI is in the input log values ($Y_{s,i}$) and
$Y_{s,i}$=value of well log i at level s
$f_i$=tool response function for well log i
$X_s$=vector of variables (porosity, etc.)
P=set of initially assumed parameters to be optimized
$\sigma_{s,i}$=error on well log i
M=number of logs plus constraints
N=number of depth levels in the zone Step 440 requires the estimation of variable T2 cut-offs. Although the activities specified at step 420 have calculated the T2 distributions for the entire length of the borehole, and the T2 cut-off points have been established for each of the core samples at step 440 the T2 cut-off times are established for any depth between a given two core samples. To resolve this and derive an accurate prediction regarding the depth and location of producible hydrocarbon, variable T2 cut-off times must be derived. One manner of estimating the T2 cut-off time at an arbitrary inlieu of depth is according to a linear arithmatic average that includes the T2 cutoff times for each lithology and the corresponding lithology volume. The correlation takes the form:

$$T2^{cutoff} = \sum_{i=1}^{L} V_i T2_i^{cutoff}$$

where
$T2^{cutoff}$=T2 cutoff of formation
L=total number of lithologies (rock types)
$V_i$=fractional volume of lithology I (calculated at step 430)
$T2_i^{cutoff}$=T2 cutoff of lithology i For example, if a formation is made of a mixture of limestone, sandstone, and dolomite, then at any depth the T2 cutoff can be calculated as:

$$T2^{cutoff} = V_{lime}T2_{lime}^{cutoff} + V_{dolo}T2_{dolo}^{cutoff} + V_{sand}T2_{sand}^{cutoff}$$

Since the present method core samples are pure or nearly pure rock types, the T2 cut-off for pure rock types has already been found at step 420.

In some cases, linear correlation is not adequate in describing the overall T2 cut-off. In such cases, more samples are required, and a more suitable correlation must be derived. It is presently believed that the linear correlation may not be as precise as otherwise when analyzing a calcerous sand deposition. Under those conditions a non-linear relationship for derived T2 cutoff times is more appropriate.

When predicting the T2 cutoff times for calcerous sand formations, the T2 cutoff times for all the core samples must still be measured. However, it is also necessary to obtain thin-section data on all of the core samples for lithology and mineralogy determination. Under these circumstances, it is believed that the total T2 cutoff time is generally related to the T2 cutoff times of the location's surrounding lithology by the following harmonic average equation:

$$\frac{1}{T2} = \frac{1}{T2_1} + \frac{1}{T2_2}$$

For example, in a lithology of the above-described type containing limestone, sandstone, and dolomite, the equation used to derive this harmonic variable T2 cutoff is believed to be:

$$\frac{1}{T2} = \frac{\alpha V_{lime}}{T2_{lime}} + \frac{\beta V_{sand}}{T2_{sand}} + \frac{\gamma V_{dolo}}{T2_{dolo}}$$

where $\alpha$, $\beta$, and $\gamma$ depend on rock relaxivity and may generally be expressed as $x_i$.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. For example, the above teachings could be adapted for use in a dedicated or general purpose computer or microprocessor. Accordingly, the scope of protection is not limited to the embodiments described herein, but is only limited by the claims which follow, the scope of which shall include all equivalents of the subject matter of the claims.

What is claimed is:

1. A method for improved geological formation evaluation, comprising:
   (a) establishing a borehole;
   (b) taking core samples from said borehole, each of said core samples being predominantly one type of rock;
   (c) determining a T2 distribution of a formation lithology surrounding said borehole and determining a T2 cutoff time for each of said core samples;
   (d) calculating the formation lithology surrounding said borehole; and
   (e) estimating a variable T2 cutoff time based on said formation lithology.

2. The method of claim 1, wherein step (c) includes inserting a Nuclear Magnetic Resonance tool into said borehole.

3. The method of claim 2, wherein the predominant rock type in each of said core samples has a concentration of greater than about 80%.

4. The method of claim 2, further comprising the determining of effective formation porocity (MPHI) and wherein said calculating step includes the use of MPHI.

5. The method of claim 1 wherein said variable T2 cutoff time is estimated by using a linear correlation to the T2 cutoff of each of said core samples.

6. The method of claim 5 wherein said linear correlation further includes the lithology volume.

7. The method of claim 1, wherein step (a) includes recording a mud log, and said core samples are taken from said borehole based at least on said mud log.

8. The method of claim 1, wherein said variable T2 cutoff time is estimated by using a non-linear correlation to the T2 cutoff of each of said core samples.

9. The method of claim 1, wherein a first of said core samples is taken from a first depth in said borehole and a second of said core samples is taken from a second depth in said borehole, and further wherein said variable T2 cutoff time includes at least one T2 cutoff time for an arbitrary depth in said borehole, said arbitrary depth being between said first depth and said second depth and not being a depth corresponding to one of said core samples.

10. The method of claim 1, further comprising:
(f) comparing said variable T2 cutoff time to said T2 distribution to establish an amount of movable fluid corresponding to a predetermined depth of said borehole.

11. The method of claim 1, wherein said variable T2 cutoff is calculated according to the correlation:

$$T2^{cutoff} = \sum_{i=1}^{L} V_i T2_i^{cutoff}$$

where
$T2^{cutoff}$=T2 cutoff of formation
L=total number of lithologies (rock types)
$V_i$=fractional volume of lithology i
$T2_i^{cutoff}$=T2 cutoff of lithology i.

12. The method of claim 1, wherein said variable T2 cutoff is calculated according to the correlation:

$$1/T2^{cutoff} = \sum_{i=1}^{L} \frac{x_i V_i}{T2_i^{cutoff}}$$

where
$T2^{cutoff}$=T2 cutoff of formation
L=total number of lithologies (rock types)
$V_i$=fractional volume of lithology i
$T2_i^{cutoff}$=T2 cutoff of lithology i
$X_i$=a constant corresponding to lithology i and depending on rock relaxivity.

13. A device that determines variable T2 cutoff times, comprising:
means for combining data from a nuclear magnetic resonance tool with other data logs to yield a composite lithology log; and
means for deriving variable T2 cutoff times based on said composite lithology log and known T2 cutoff values.

14. The device of claim 13, wherein said known T2 cutoff values are based on wellbore core samples.

15. The device of claim 14, wherein said wellbore core samples are at least 80% purity.

16. The device of claim 14, wherein said wellbore core samples are predominantly one type of rock.

17. The device of claim 13, wherein said means for deriving uses a linear correlation based on lithology volume.

18. The device of claim 13, wherein said means for deriving uses a non-linear correlation based on lithology volume.

19. The device of claim 13, wherein said means for combining data and said means for deriving are a computer.

20. A method to determine a variable T2 cutoff time, comprising:
(a) determining a first T2 cutoff time corresponding to a first lithology at a first depth in a borehole, and a second T2 cutoff corresponding to a second lithology at a second depth in a borehole;
(b) measuring an arbitrary lithology that includes said first lithology and said second lithology, said arbitrary lithology corresponding to an arbitrary depth;
(c) calculating a variable T2 cutoff time for said arbitrary lithology, said variable T2 cutoff time including an arbitrary T2 cutoff time corresponding to said arbitrary depth of said arbitrary lithology, said arbitrary T2 cutoff time being dependent upon said first T2 cutoff time, said second T2 cutoff time, and the composition of said arbitrary lithology at said arbitrary depth.

21. The method of claim 20, wherein said arbitrary lithology includes a plurality of rock types and said calculating step is dependent on the volume of each rock type in said arbitrary lithology.

22. The method of claim 21, wherein said calculating step is linear.

23. The method of claim 22, wherein said calculating step is according to the equation:

$$T2^{cutoff} = \sum_{i=1}^{L} V_i T2_i^{cutoff}$$

where
$T2^{cutoff}$=T2 cutoff of formation
L=total number of lithologies (rock types)
$V_i$=fractional volume of lithology i
$T2_i^{cutoff}$=T2 cutoff of lithology i.

24. The method of claim 21, wherein said calculating step is non-linear.

25. The method of claim 24, wherein said calculating step is according to the equation:

$$1/T2^{cutoff} = \sum_{i=1}^{L} \frac{x_i V_i}{T2_i^{cutoff}}$$

where
$T2^{cutoff}$=T2 cutoff of formation
L=total number of lithologies (rock types)
$V_i$=fractional volume of lithology i
$T2_i^{cutoff}$=T2 cutoff of lithology i
$X_i$=a constant corresponding to lithology i and depending on rock relaxivity.

* * * * *